(12) United States Patent
Ducharme

(10) Patent No.: US 8,142,431 B2
(45) Date of Patent: Mar. 27, 2012

(54) SPHINCTEROTOME CUTTING WIRE IMPROVEMENT

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1249 days.

(21) Appl. No.: 11/770,386

(22) Filed: Jun. 28, 2007

(65) Prior Publication Data

US 2009/0005778 A1 Jan. 1, 2009

(51) Int. Cl.
*A61B 18/14* (2006.01)
(52) U.S. Cl. .............. 606/47; 606/41; 606/45
(58) Field of Classification Search .............. 606/41, 606/45–47
See application file for complete search history.

(56) References Cited

U.S. PATENT DOCUMENTS

| | | | |
|---|---|---|---|
| 4,181,131 A | | 1/1980 | Ogiu |
| 4,485,812 A | * | 12/1984 | Harada et al. ............. 606/47 |
| 4,582,067 A | * | 4/1986 | Silverstein et al. ........ 600/455 |
| 5,743,905 A | * | 4/1998 | Eder et al. ................. 606/32 |
| 5,746,746 A | * | 5/1998 | Garito et al. .............. 606/41 |
| 5,810,807 A | * | 9/1998 | Ganz et al. ................ 606/47 |
| 5,902,272 A | | 5/1999 | Eggers et al. |
| 6,021,355 A | | 2/2000 | Shchervinsky |
| 6,030,381 A | * | 2/2000 | Jones et al. ............... 606/41 |
| 6,712,817 B1 | | 3/2004 | Goto et al. |
| 2005/0149015 A1 | | 7/2005 | Durgin et al. |

OTHER PUBLICATIONS

Webpages from the Para Tech Coating company (www.parylene.com) dated Oct. 2006.*

* cited by examiner

*Primary Examiner* — Linda Dvorak
*Assistant Examiner* — Daniel Fowler
(74) *Attorney, Agent, or Firm* — Brinks Hofer Gilson & Lione

(57) ABSTRACT

A sphincterotome having a portion of its drive wire coated with a material selected from poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof. The coating preferably provides an electroinsulated coating on a portion of the drive wire exposed outside the sphincterotome shaft such that a non-electroinsulated portion of the exposed drive wire may be targeted more specifically to tissue desired to be cut.

28 Claims, 7 Drawing Sheets

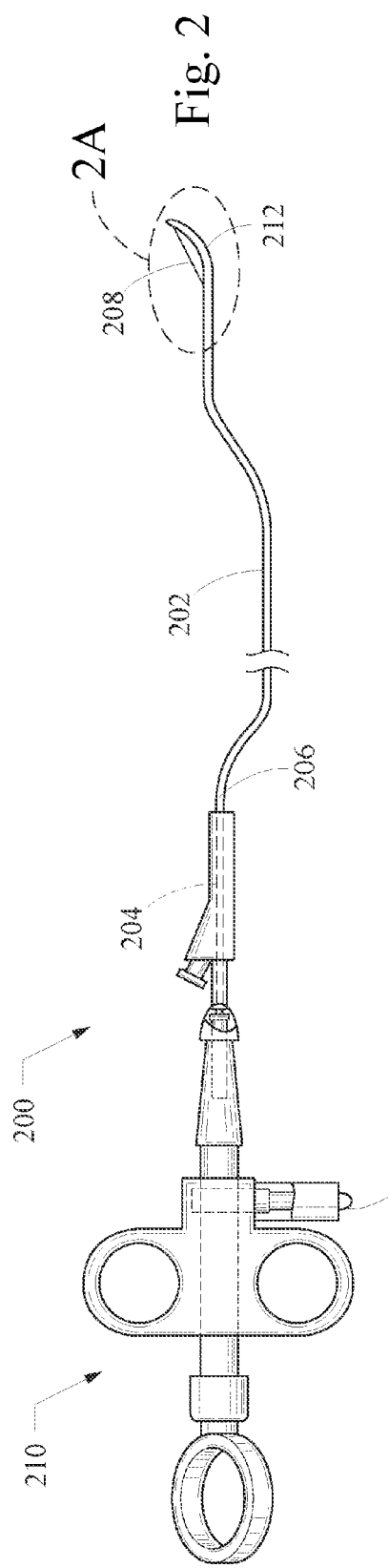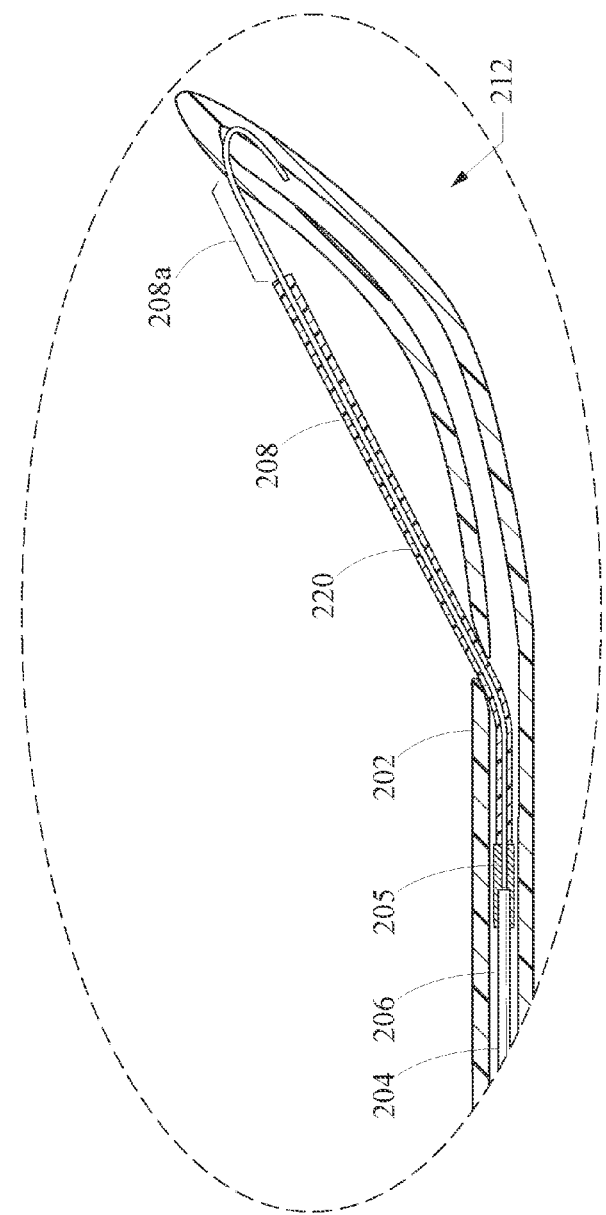

SPHINCTEROTOME CUTTING WIRE IMPROVEMENT

BACKGROUND OF THE INVENTION

The present device relates to medical devices, and specifically to improvements to devices such as sphincterotomes, also known as papillotomes.

In endoscopic, or other minimally invasive surgery, generically referred to herein as endoscopic surgery, a sphincterotome may be used in conjunction with an endoscope to provide surgical cutting inside a patient. Specifically, a sphincterotome is used during certain procedures to make an incision in a sphincter. For example, a common treatment of cholecystitis includes the removal of gallstones from the common bile duct. This is frequently done endoscopically with the use of a duodenoscope. The common bile duct proceeds from the junction of the common hepatic duct with the cystic duct, which is open to the gall bladder, and merges with the pancreatic duct, forming the ampulla of Vater, which itself opens into the duodenum at the papilla of Vater. The sphincter of Oddi is a muscular ring that controls passage of fluid from the ampulla of Vater into the duodenum. For removal of gallstones in an endoscopic procedure, access to the common bile duct for removal of gallstones is eased using a sphincterotome to incise or sever the sphincter of Oddi. The sphincterotome is introduced through the duodenoscope and guided through the duodenum to the common bile duct. Once the sphincterotome is guided into the sphincter, its cutting element, commonly a needle knife or cutting wire, is used to incise the sphincter, and thereby improve access to the bile duct and impacted gallstones.

Another example of a common procedure utilizing a sphincterotome is endoscopic retrograde cholangiopancreatography (ERCP), a diagnostic visualization technique used for variety of clinical applications. In this procedure, a contrast fluid such as a radio-opaque dye is introduced through a tube into the ampulla of Vater. A sphincterotome is often employed to provide access through the sphincter of Oddi in the same manner as described above. ERCP is often used in diagnosis of cholecystitis, as well as in the diagnosis and treatment of other conditions of the pancreatic and common bile ducts and related structures.

As illustrated in FIG. 1, a typical sphincterotome 100 includes a polymer tubular shaft 102 made of PTFE (polytetrafluoroethylene) or another flexible material. An electroconductive filament 104, also called a drive wire, is disposed in a lumen 106 running through the shaft 102. The distal end of the filament 104 is connected or anchored to the distal end of the shaft 102. A short segment of the electroconductive filament 104 near the distal end thereof is disposed outside of the shaft 102 for use as an electrocautery cutting wire 108. The proximal end of filament 104 is connected to the proximal handle assembly 110 such that actuation of the handle assembly 110 partially retracts (i.e., pulls in a proximal direction) the filament 104 relative to the polymer shaft 102. This actuation results in the distal end of shaft 102 bowing to form an arc 112, with the exposed filament forming a secant of the arc 112 so as to form a cutting wire 108. Electric current passed through the filament 104 from an electrode 114 in the handle assembly 110 enables the cutting wire 108 to act as an electrosurgical cutting element that may be used effectively to cut and cauterize tissue, such as the sphincter of Oddi in the example procedures described above.

One problem that may occur during use of a sphincterotome is that tissue adjacent the sphincter of Oddi may inadvertently be cut. Specifically, the papillary tissue around the sphincter often protrudes as a folded surface. During a sphincterotomy, it is most preferable to incise only the desired tissue of the sphincter to permit cannulation thereof. However, the adjacent papillary folds may inadvertently be cut or otherwise damaged by a portion of the cutting wire 108 adjacent the portion thereof that is actually incising the sphincter. Another problem that can occur is that current may arc from the exposed cutting wire to the endoscope or another structure. If this occurs, the cutting wire may break, rendering the sphincterotome useless, and potentially even releasing one or more wire fragments, which may pose an injury risk. For these reasons, it is desirable to have only a small cutting wire portion exposed such that it can be used in a targeted fashion for a sphincterotomy. Physical structural constraints of the sphincterotome prevent this from being accomplished by having only a small enough arc 112 to target the cutting wire in this manner. As a result, some sphincterotomes have included a coated portion of the cutting wire. These devices typically use PTFE or another polymer in the form of a sleeve. These coating sleeves also suffer from shortcomings. For example, during ordinary assembly and use, the sleeve may be nicked or split (e.g., by contact with an elevator of an endoscope), or may migrate longitudinally in a manner that exposes the wire and negates the intended insulating effect. This type of sleeve coating also increases the outer diameter of the cutting wire. Therefore, there is a need for a sphincterotome wire coating that provides desirable electro-insulation, resists damage, and does not significantly increase cutting wire diameter.

BRIEF SUMMARY OF THE INVENTION

Embodiments of the present invention include a polymeric coating that addresses the aforementioned needs by providing a thin but durable electroinsulative coating for a sphincterotome cutting wire.

In one aspect, the present invention may include a sphincterotome that has a cutting wire including a coated portion. The coated portion may includes a parylene coating such as a coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof.

In another aspect, the present invention may include a sphincterotome that has a cutting wire including a coated portion. The coated portion includes a bio-compatible polymeric coating means for providing a generally uniform bonded surface covering having a static coefficient of friction below about 0.4, for bonding to the cutting wire, and for providing an electroinsulative layer.

In still another aspect, the present invention may include a method of making a sphincterotome having a partially electroinsulated cutting wire. The method includes providing a sphincterotome cutting wire, then coating at least a portion of the cutting wire with a polymeric coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof. The method also includes assembling the cutting wire to a sphincterotome assembly.

In still yet another aspect, the present invention may include a method of cannulating a constricted structure by providing a sphincterotome including a shaft, a drive wire disposed longitudinally through a lumen of said shaft except for a distal cutting wire portion of the drive wire exposed outside the shaft, and a handle configured to tension the drive wire relative to the shaft in a manner that arcs a distal shaft portion. The distal drive wire portion may include an electroinsulated region and a non-electroinsulated cutting region immediately adjacent thereto. The electroinsulated region may include a coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof. The method also includes directing a distal sphincterotome region to a constricted structure in need of cannulation, contacting the constricted structure with the cutting region, and directing an electrical current to the cutting region.

BRIEF DESCRIPTION OF THE DRAWINGS

FIG. 2 depicts a sphincterotome embodiment of the present invention, including a coated wire portion.

DETAILED DESCRIPTION

Figure 1:
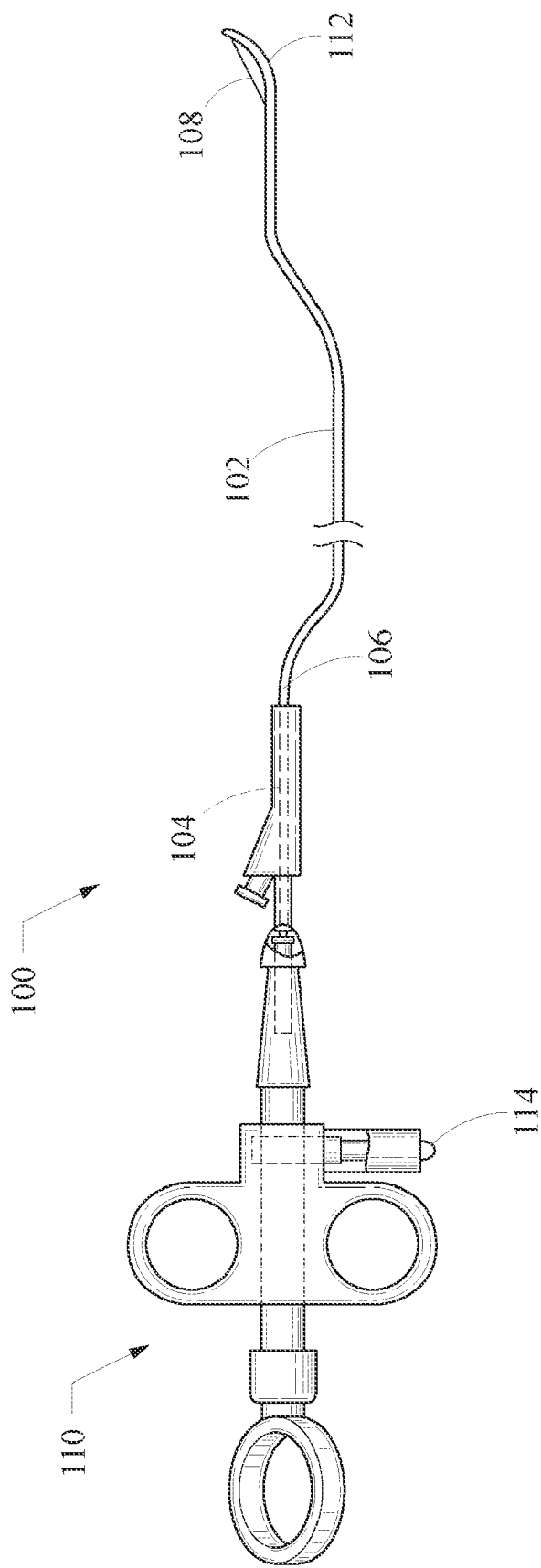
FIG. 1 shows a typical sphincterotome.

The following disclosure describes an embodiment of a sphincterotome according to the present invention including an electroconductive wire that includes a drive wire portion and cutting wire portion having an insulated portion. Those of skill in the art will appreciate that variations and equivalents of the described embodiment may be practiced within the scope of this application.

FIG. 2 depicts a sphincterotome 200 of the present invention, which includes a polymer tubular shaft 202 that may be constructed, for example, of PTFE or similarly suitable material. An electroconductive drive wire 204 extends longitudinally from a handle assembly 210 through a lumen 206 that extends through a major length of the shaft 202. The distal-most end of the drive wire 204 is attached by a soldered-on cannula 205 to an electrocautery cutting wire 208 near the distal end of the shaft 202. In one preferred embodiment, the cutting wire 208 has a smaller outer diameter than the drive wire 204. A short length of the cutting wire 208 near the distal end of the shaft 202 extends outside of the shaft 202. In a non-actuated state of the sphincterotome, the drive wire 204 is generally parallel with a longitudinal axis of the shaft 202. A proximal end portion of drive wire 204 preferably is connected to the proximal handle assembly 210 such that actuation of the handle assembly 210 pulls the drive wire 204 in a proximal direction relative to the shaft 202. This actuation results in a distal portion of the shaft 202 bowing to form an arc 212, with the exposed cutting wire portion 208 forming a secant of the arc 212 so as to form a transecting cutting wire portion 208.

A portion of the cutting wire 208 is coated with a polymeric coating 220. For the sake of clarity in the figures, the distal region of the shaft 202 is shown magnified in longitudinal cross-section in FIG. 2A, and the thickness of the coating 220 is not shown to scale. Additionally, for clarity in the figures, a wire guide lumen of the shaft is not shown, although those of skill in the art that many sphincterotomes include a wire guide lumen configured for short-wire and/or long-wire applications. A preferred coating of the present invention may be between a fraction of a micron and several thousandths of an inch in thickness. A preferred coating also preferably includes a low coefficient of friction and is electroinsulative. A cutting portion 208a of the transecting wire 208 remains uncoated. In this manner, electric current passed through the drive wire 204 from an electrode 214 in the handle assembly 210 enables the cutting portion 208a to act as an electrosurgical cutting element that may be used effectively to cut and cauterize tissue (such as, for example, the sphincter of Oddi during a sphincterotomy procedure providing access to the biliary tree).

The cutting portion 208a is shorter than the transecting wire portion of the cutting wire 208 that is exposed out of the lumen 206. The coating 220 provides electroinsulation such that the cutting portion 208a may be used in a highly targeted manner to incise only desired tissue with minimal risk to adjacent tissue. For example, a sphincterotome of the present invention may include a 35 cm cutting wire having an exposed transecting wire portion of about 20, 25, or 30 mm in length, with about 8 to about 10 mm of that length being configured for use as a cutting portion and not covered with an electroinsulative coating. In such a sphincterotome embodiment, the coating may cover about 5 cm of the wire's length. This coating length provides for a more proximal coated portion of the cutting wire extending well into lumen, which provides a safety feature. In many sphincterotomy procedures, a cutting portion of about 8 to about 10 mm provides an ideal length for incision of a sphincter while minimizing likelihood of damage to adjacent tissues. A distal-most portion of the cutting wire mounted into the shaft of the sphincterotome in a manner known or developed in the art may be coated or uncoated.

We have discovered a coating substance and method that work exceptionally well for a sphincterotome wire application. A highly preferred coating includes parylene-N (poly-p-xylylene). When used in a manner according to the present invention, this coating requires less materials, provides superior electroinsulation and durability as well as cost advantages as compared to existing coatings such as, for example, PTFE. Other xylylene polymers, and particularly parylene polymers, may also be used as a coating within the scope of the present invention, including, for example, 2-chloro-p-xylylene (Parylene C), 2,4-dichloro-p-xylylene (Parylene D), poly(tetraflouro-p-xylylene), poly(carboxyl-p-xylylene-co-p-xylylene), fluorinated parylene, or parylene HT® (a copolymer of per-fluorinated parylene and non-fluorinated parylene), alone or in any combination. Preferred coatings of the present will include the following properties: low coefficient of friction (preferably below about 0.5, more preferably below about 0.4, and most preferably below about 0.35); very low permeability to moisture and gases; fungal and bacterial resistance; high tensile and yield strength; high conformality (ready application in uniform thickness on all surfaces, including irregular surfaces, without leaving voids); radiation resistance (no adverse reaction under fluoroscopy); bio-compatible/bio-inert; acid and base resistant (little or no damage by acidic or caustic fluids); ability to be applied by chemical vapor deposition bonding/integrating to wire surface (bonding is intended to contrast to, for example, fluoroethylenes that form surface films that are able to be peeled off an underlying wire); and high dielectric strength. Parylene coatings, in particular, exhibit these qualities. See, for example, Table 1.

TABLE 1

| Typical Parylene Properties | | | | |
|---|---|---|---|---|
| | Parylene N | Parylene C | Parylene D | Parylene HT |
| Typical Physical & Mechanical Properties | | | | |
| Coefficient of friction: static | 0.25 | 0.29 | 0.33 | 0.145 |
| dynamic | 0.25 | 0.29 | 0.31 | 0.13 |
| Melt point (° C.) | 420 | 290 | 380 | 7500 |
| Typical Electrical Properties | | | | |
| Dielectric strength, short time (Volts/mil at 1 mil) | 7,000 | 5,600 | 5,500 | 5,400 |
| Dielectric constant: 60 Hz | 2.65 | 3.15 | 2.84 | 2.21 |
| 1,000 Hz | 2.65 | 3.1 | 2.82 | 2.2 |
| 1,000,000 Hz | 2.65 | 2.95 | 2.8 | 2.17 |

In a preferred embodiment of the present invention, the coating 220 is applied to the drive wire 204 by chemical vapor deposition ("CVD", which may include a plasma-assisted CVD process). Chemical vapor deposition is a well-known process in the art of electronic circuitry that is well-adapted for applying a coating, such as—for example—a parylene coating, to a wire. The process smoothly and uniformly applies the coating to the wire around its circumferential surface. A coated drive wire using a parylene coating presents advantages in coating durability, cost savings, and desirable outer diameter, while providing a coating with excellent lubricity (low friction) and electroinsulative qualities. In contrast with prior art coatings, a bonded coating of the present invention will not split or peel away from the wire due to frictional or traumatic contact with another surface such as, for example, an elevator or wire lock mechanism of an endoscope.

A preferred drive wire of the present invention is electroconductive and may be constructed of stainless steel, nitinol, or another electroconductive material within the scope of the present invention. In another embodiment (not shown) a single wire may be used wherein a distal portion of the drive wire may be used as a cutting wire. In such an embodiment, the cutting wire portion of the drive wire may include a reduced diameter. Like the embodiment described with reference to FIGS. 2-2A, a reduced outer diameter of the cutting wire portion may allow it to form a more targeted cutting surface. Of course, the outer diameter of the drive wire may be substantially the same as that of the cutting wire portion, whether they are seamlessly continuous or connected by a cannula, weld, or some other connecting means.

Figure 3A:
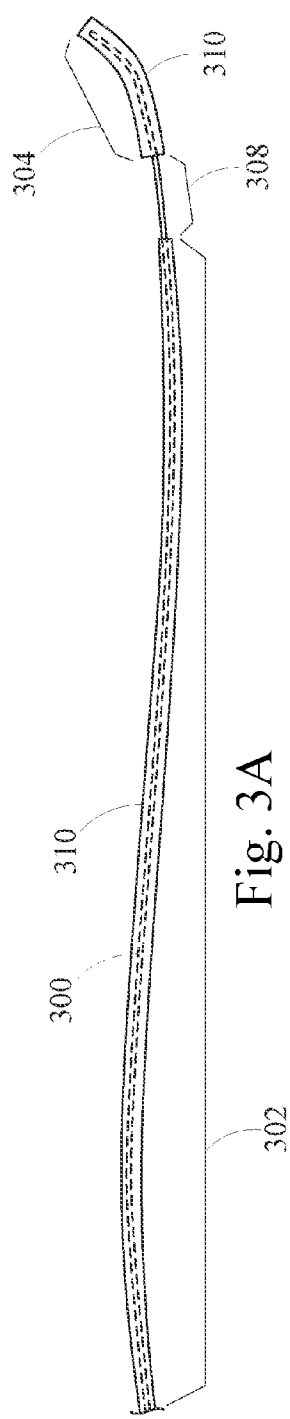
FIGS. 3A-3D show a method of making a sphincterotome with a coated wire.
Figure 3B:
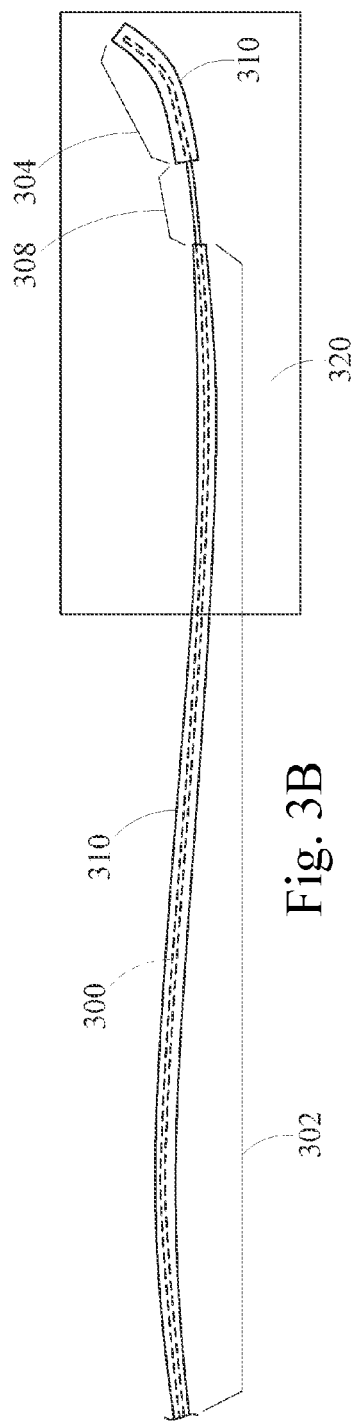

In a method of the present invention, a sphincterotome may be provided using a coated drive wire. One embodiment of such a method is illustrated with reference to FIGS. 3A-3D. As shown in FIG. 3A, a standard drive wire 300 is provided and proximal and distal portions 302, 304 are coated with a removable protective masking 310. Proximal portion 302 includes a major proximal length of the wire 300, distal portion 304 includes the distal end of the wire 300, and an unmasked wire portion 308 is disposed therebetween. Some or all of the unmasked wire portion 308 may be ground or otherwise treated to reduce its outer diameter such that a cutting wire portion thereof presents a smaller cross-sectional area for cutting as compared to the rest of the drive wire length. The removable protective masking 310 is provided to protect the drive wire 300 during the insulative coating application process. As depicted in FIG. 3B, an insulative coating 320 including a parylene or other appropriate coating is then applied using a chemical vapor deposition process. In this embodiment, the insulative coating 320 is applied to the unmasked wire portion 308 to form an electroinsulated wire portion 308.

Figure 3C:
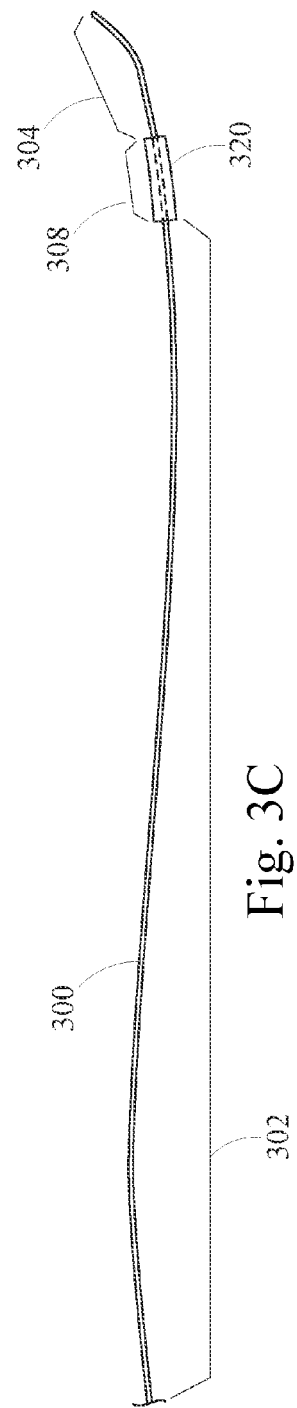
Figure 3D:
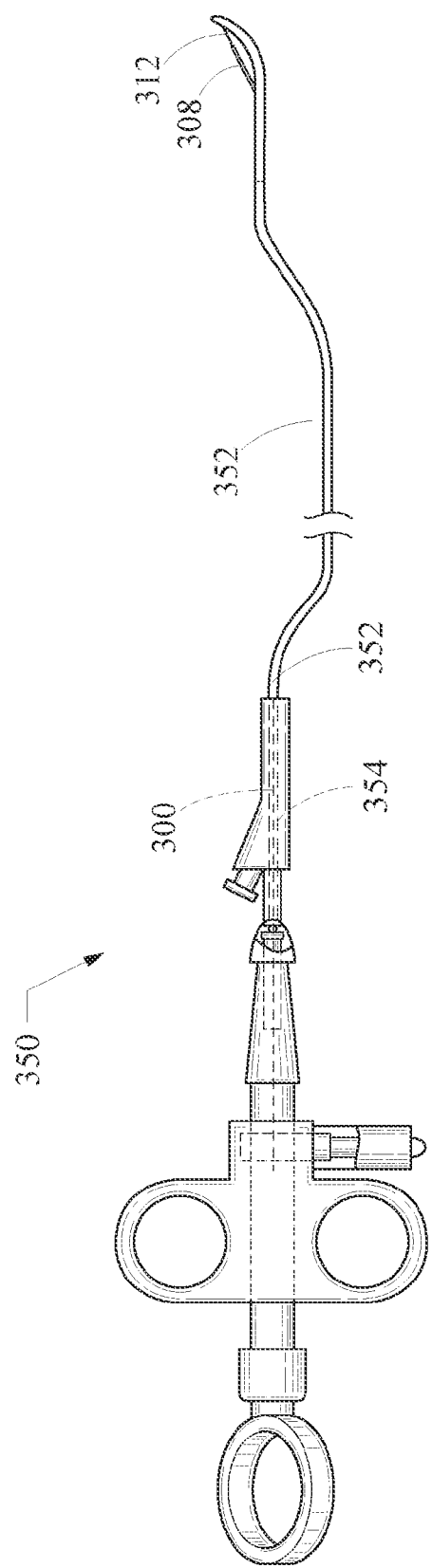

Then, as shown in FIG. 3C, the drive wire 300 may have the removable protective masking 310 removed. The drive wire 300 may then be assembled to a sphincterotome 350. FIG. 3D shows that when the drive wire 300 is assembled to the sphincterotome 350, the electroinsulated wire portion 308 extends outside the drive wire lumen 354 of the sphincterotome shaft 352. The non-electroinsulated portion of the drive wire 300 that is exposed outside the shaft 352 is immediately adjacent the distal tip 354 of the sphincterotome 350. In this manner, as described above, the short, non-electroinsulated length of the drive wire 300 is exposed for use as a cutting wire portion 312 that can function in a more targeted fashion than a wholly non-insulated cutting wire.

Coating the wire in the targeted fashion of the described embodiment of a method will provide a desired electroinsulative coating, while also providing a minimal use of the electroinsulative coating and attendant cost savings. Those of skill in the art will appreciate that, in other embodiments, a greater length—up to and including the entire length—of the drive wire may be coated with an electro-insulative coating. In these alternative embodiments, the thinness and uniformity of the coating, whether applied by chemical vapor deposition or another process preferably are consistent along the wire length, but most preferably provide an integrity-maintaining coating in a region of the drive wire that is to be exposed outside the sphincterotome shaft but not intended to be used for cutting (specifically that region of the drive wire immediately adjacent the cutting wire portion and exposed outside the sphincterotome lumen during normal operation). The steps of assembling a drive wire to a sphincterotome are generally known in the art.

Figures 5A, 5B, 5C:
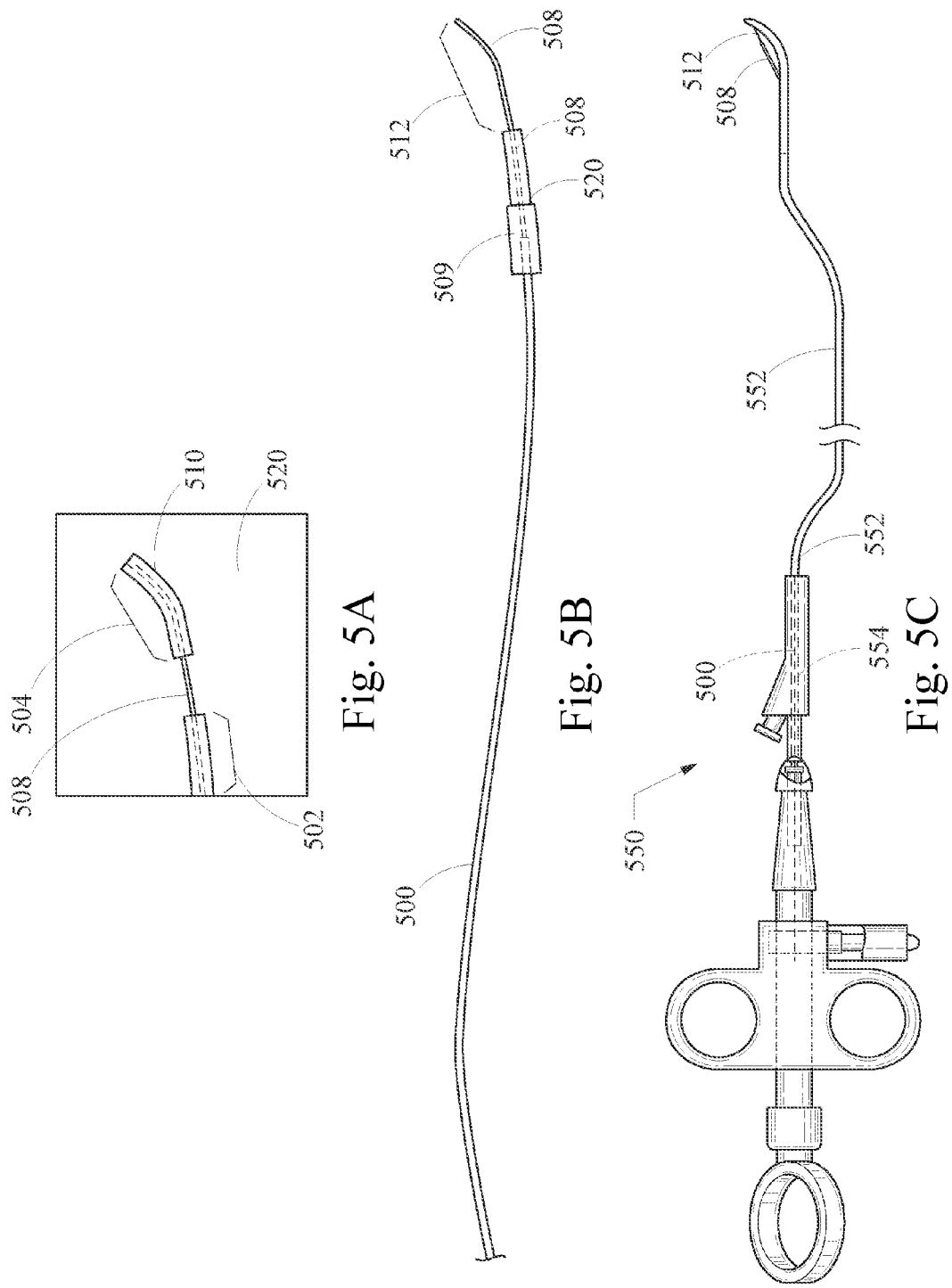
FIGS. 5A-5C show another method of making a sphincterotome with a coated wire.

Another embodiment of such a method is illustrated with reference to FIGS. 5A-5C. As shown in FIG. 5A, a cutting wire 508 is provided and proximal and distal portions 502, 504 thereof are coated with a removable protective masking 510. The removable protective masking 510 is provided to cover the cutting wire 508 during the insulative coating application process, preventing a distal portion 512 from being coated. Then, an insulative coating 520 including a parylene or other appropriate coating is then applied using a chemical vapor deposition process. In this embodiment, the insulative coating 520 is applied to the unmasked portion of the cutting wire 508.

As depicted in FIG. 5B, a drive wire 500 may then be provided and attached to the cutting wire 508 by a cannula 509 or another connecting means (not shown to scale). The drive wire 500 may also have the removable protective masking 510 removed. The drive wire 500 may then be assembled to a sphincterotome 550. FIG. 5C shows that when the drive wire 500 is assembled to the sphincterotome 550, the electroinsulated wire portion 508 extends outside the drive wire lumen 554 of the sphincterotome shaft 552. The non-electro-insulated portion (512) of the cutting wire 508 that is exposed outside the shaft 552 is immediately adjacent the distal tip 554 of the sphincterotome 550. In this manner, as described above, the short, non-electroinsulated length 512 of the drive wire 500 will be exposed for use as a cutting wire portion 512 that can function in a more targeted fashion than a wholly non-insulated cutting wire. For the sake of clarity in the figures, the cannula 509 and the coating 520 are not shown to scale. A preferred coating of the present invention may be between a fraction of a micron and several thousandths of an inch in thickness.

Coating the wire in the targeted fashion of the described embodiment of a method will provide a desired electroinsulative coating, while also providing a minimal use of the electroinsulative coating and attendant cost savings. Those of skill in the art will appreciate that, in other embodiments, a greater length—up to and including the entire length—of the drive wire may be coated with an electro-insulative coating. In these alternative embodiments, the thinness and uniformity of the coating, whether applied by chemical vapor deposition or another process preferably are consistent along the wire length, but most preferably provide an integrity-maintaining coating in a region of the drive wire that is to be exposed outside the sphincterotome shaft but not intended to be used for cutting (specifically that region of the drive wire immediately adjacent the cutting wire portion and exposed outside the sphincterotome lumen during normal operation). The steps of assembling a drive wire to a sphincterotome are generally known in the art.

Figure 4A:
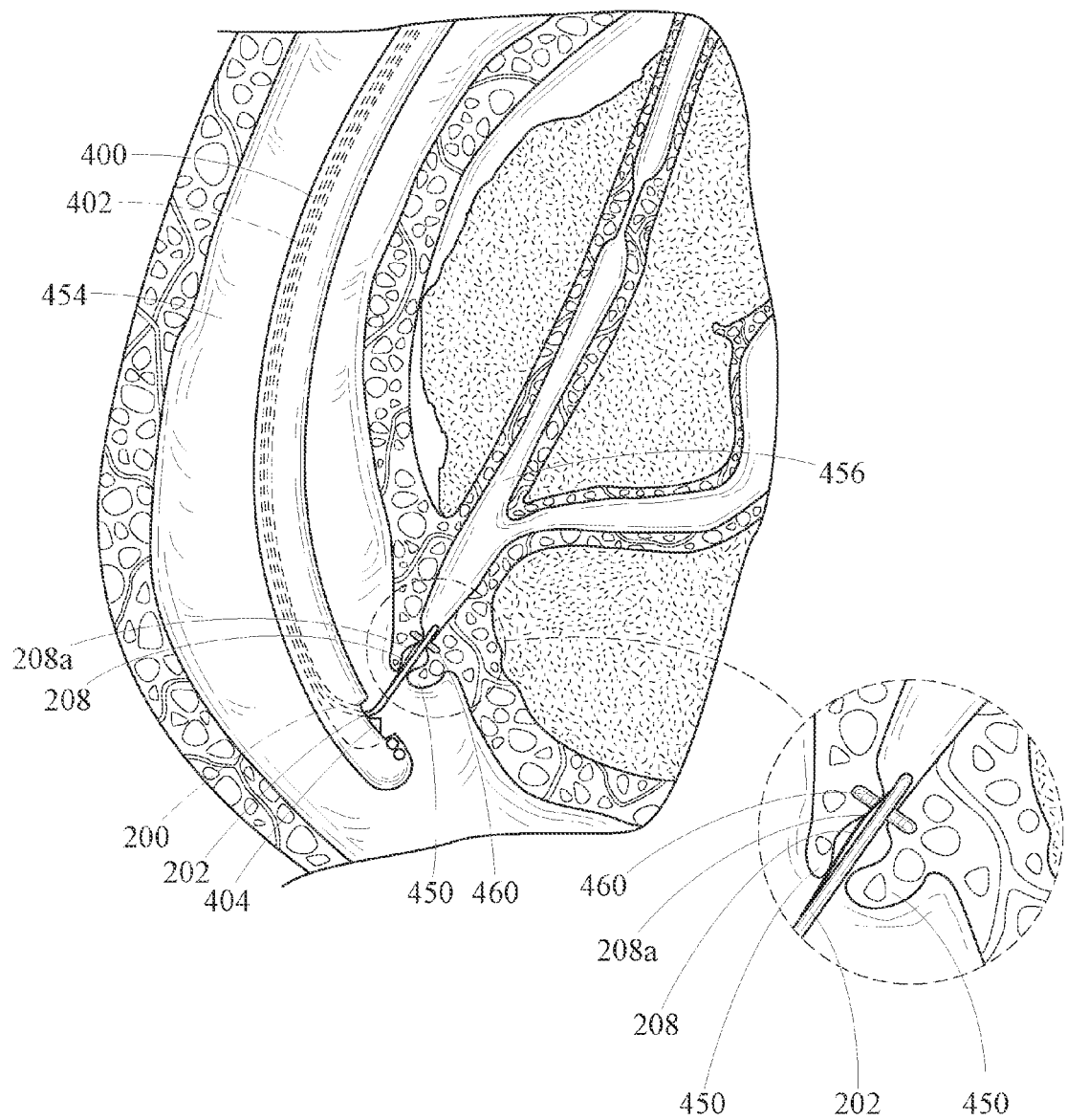
FIGS. 4A-4B illustrate a method of using a sphincterotome of the present invention.
Figure 4B:
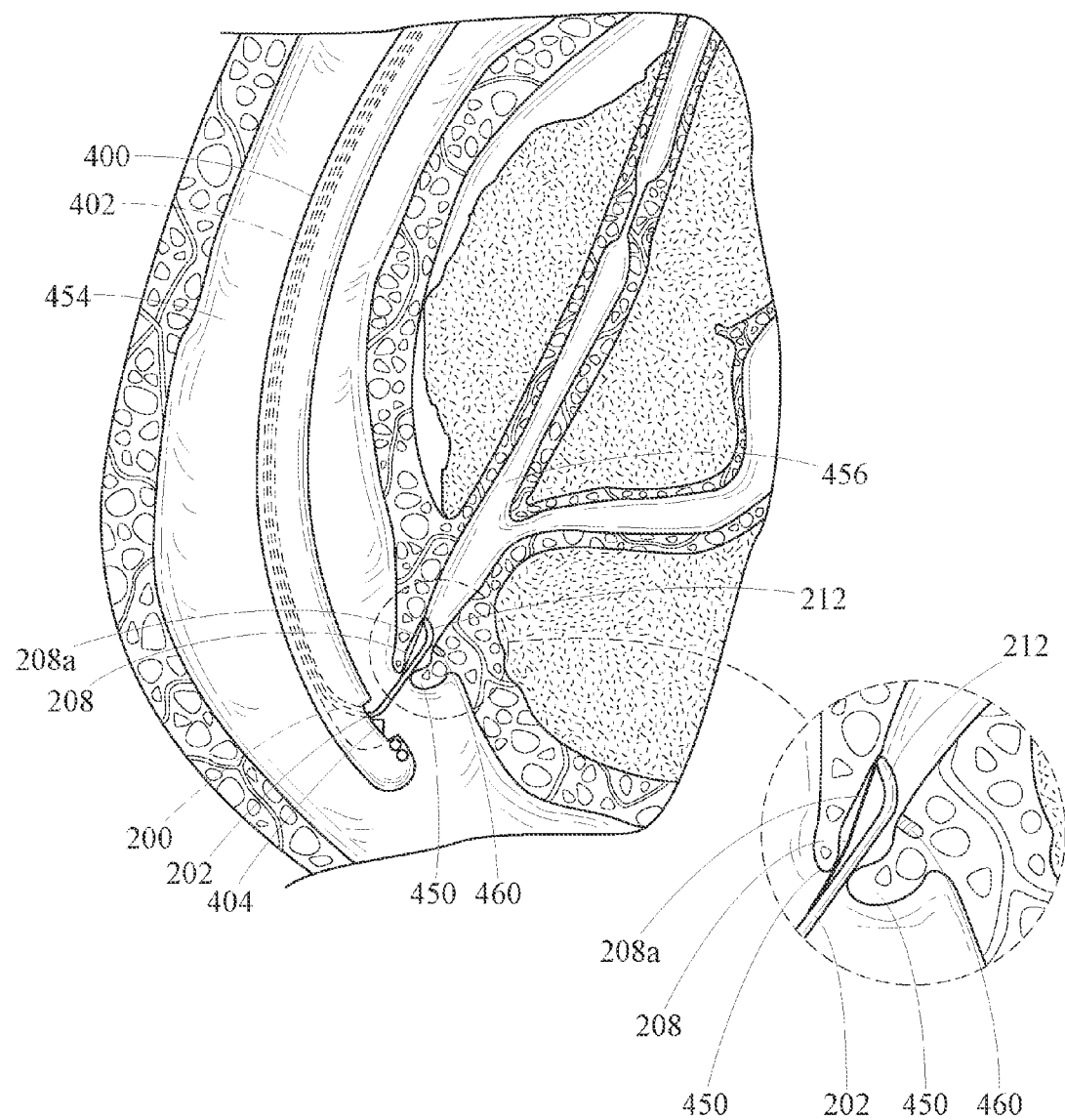

A method of using a sphincterotome of the present invention for cannulating a constricted structure is shown in an embodiment of a sphincterotomy and described here with reference to FIGS. 4A-4B, with reference being made to the sphincterotome embodiment of FIG. 2. As shown in FIG. 4A, the shaft 202 of a sphincterotome 200 (a proximal portion of which, including the handle, is not shown) is directed through a working channel 402 of an endoscope 400. The distal end of the sphincterotome 200 is angled by an elevator 404 of the endoscope 400 to a location adjacent the papilla of Vater 450 where the common bile duct 456 meets the duodenum 454. FIG. 4A also shows the distal end portion of the sphincterotome 200 being directed through the papillary folds 450 and into the sphincter of Oddi 460 until the cutting portion 208a of the drive wire contacts the sphincter 460. As shown in FIG. 4B, the sphincterotome 200 can then be actuated both mechanically and electrically. The mechanical actuation includes a typical sphincterotome method of actuating the handle (not shown) to tension the drive wire relative to the shaft 202, thereby forming an arc 212 of the distal shaft 212, with the transecting wire 208 portion of the drive wire forming a secant thereof. The cutting portion 208a of the transecting wire 208 contacts the sphincter 460, and the electrical actuation (which includes directing an electrical current through the drive wire) provides for coagulative cutting of the sphincter 460 by the cutting portion 208a.

Persons of skill in the art will appreciate that other arrangements of the coating described herein may be practiced within the scope of the present invention. Certain materials and methods appropriate for use with the foregoing embodiments of the present invention but not explained in detail herein will be readily apparent to those skilled in the art (such as, for example, using a coated wire of the present invention with a multi-lumen sphincterotome). It is therefore intended that the foregoing detailed description be regarded as illustrative rather than limiting, and that it be understood that it is the following claims, including all equivalents, that are intended to define the spirit and scope of this invention.

I claim:
1. A sphincterotome, comprising:
a cutting wire comprising a coated portion,
wherein said coated portion comprises a coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof.
2. The sphincterotome of claim 1, wherein the coating comprises poly-p-xylylene.
3. The sphincterotome of claim 1, wherein the coating is disposed on a major length of the cutting wire.
4. The sphincterotome of claim 1, wherein the coating is bonded with a surface of the cutting wire and is substantially uniformly distributed thereupon.
5. The sphincterotome of claim 1, wherein the coating is disposed upon a proximal cutting wire portion, and not upon a distal drive wire portion.
6. The sphincterotome of claim 1, wherein cutting wire further comprises a drive wire.
7. The sphincterotome of claim 6, wherein the drive wire comprises a second wire having a greater outer diameter than the cutting wire and being attached to a proximal end of the cutting wire.
8. The sphincterotome of claim 1, further comprising a handle operatively connected to an elongate shaft and a drive wire, said drive wire being connected to the cutting wire.
9. The sphincterotome of claim 1, further comprising:
a handle having a first handle portion and a second handle portion;
an elongate shaft having a lumen and being attached to the first handle portion;
a drive wire attached to the second handle portion and extending through said lumen, said drive wire being connected to the cutting wire; and
wherein the first and second handle portions are slidably disposed relative to each other such that a motion of one relative to the other slidingly actuates the drive wire relative to the shaft.
10. The sphincterotome of claim 9, further comprising:
a distal cutting wire end being affixed adjacent a distal elongate shaft end; and
an uncoated cutting wire portion of about 8 to about 10 mm in length adjacent the distal cutting wire end.
11. The sphincterotome of claim 10, wherein the coated cutting wire portion is immediately proximal of the uncoated cutting wire portion and the coated cutting wire portion extends into the lumen.
12. The sphincterotome of claim 1, wherein a distal uncoated cutting wire portion comprises about 8 to about 10 mm in length of the cutting wire.
13. The sphincterotome of claim 1, wherein the cutting wire is about 35 cm in length, the coated portion comprises about 5 cm of that length, and a distal uncoated cutting wire portion comprises about 8 to about 10 mm of that length.
14. A sphincterotome, comprising:
a cutting wire comprising a coated portion,
wherein said coated portion comprises a bio-compatible polymeric coating means for providing a generally uniform bonded surface covering having a static coefficient of friction below about 0.4, for bonding to the cutting wire, and for providing an electroinsulative layer.

15. The sphincterotome of claim 14, wherein the polymeric coating means comprises a polymer selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof.

16. The sphincterotome of claim 15, wherein the polymeric coating means comprises poly-p-xylylene.

17. The sphincterotome of claim 14, further comprising a handle operatively connected to an elongate shaft and a drive wire, said drive wire being connected to the cutting wire.

18. The sphincterotome of claim 14, further comprising:
a handle having a first handle portion and a second handle portion;
an elongate shaft attached to the first handle portion;
a drive wire attached to the second handle portion, said drive wire being connected to the cutting wire; and
wherein the first and second handle portions are slidably disposed relative to each other such that a motion of one relative to the other slidingly actuates the drive wire relative to the shaft.

19. A method of making a sphincterotome having a partially electroinsulated cutting wire, said method comprising the steps of:
providing a sphincterotome cutting wire;
coating at least a portion of the cutting wire with a polymeric coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof; and
assembling the cutting wire to a sphincterotome assembly.

20. The method of claim 19, wherein the step of providing a sphincterotome cutting wire further comprises masking at least a first portion of the cutting wire, and the step of coating at least a portion of the cutting wire comprises coating a second portion of the cutting wire that is not masked.

21. The method of claim 19, wherein the step of coating at least a portion of the cutting wire comprises using a chemical vapor deposition process to apply a coating.

22. The method of claim 19, wherein the coating comprises poly-p-xylylene.

23. The method of claim 19, wherein the coating comprises a parylene.

24. The method of claim 19, wherein the cutting wire further comprises a drive wire.

25. A method of cannulating a constricted structure, said method comprising the steps of:
providing a sphincterotome comprising a shaft, a drive wire disposed longitudinally through a lumen of said shaft except for a distal cutting wire portion of the drive wire exposed outside said shaft, and a handle configured to tension the drive wire relative to the shaft in a manner that arcs a distal shaft portion,
wherein the distal cutting wire portion comprises an electroinsulated region and a non-electroinsulated cutting region immediately adjacent thereto, said electroinsulated region comprising a coating selected from the group consisting of poly-p-xylylene, 2-chloro-p-xylylene, 2,4-dichloro-p-xylylene, poly(tetraflouro-p-xylylene), poly(carboxyl-p-xylylene-co-p-xylylene), fluorinated parylene, parylene HT, and any combination thereof;
directing a distal sphincterotome region to a constricted structure in need of cannulation;
contacting the constricted structure with the cutting region; and
directing an electrical current to the cutting region.

26. The method of claim 25, wherein the coating comprises poly-p-xylylene.

27. The method of claim 25, wherein the constricted structure is immediately adjacent material desired to remain uncut, and the electroinsulated region contacts the adjacent material while the cutting region does not.

28. The method of claim 25, wherein the directing step comprises providing an endoscope comprising a working channel and directing the sphincterotome through the working channel.

* * * * *